US007189409B2

(12) United States Patent
Pirhonen et al.

(10) Patent No.: US 7,189,409 B2
(45) Date of Patent: Mar. 13, 2007

(54) BONE GRAFTING MATERIAL, METHOD AND IMPLANT

(75) Inventors: Eija Pirhonen, Tampere (FI); Loredana Moimas, Tampere (FI); Franz Weber, Singen (DE)

(73) Assignee: Inion Ltd., Tampere (FI)

( * ) Notice: Subject to any disclaimer, the term of this patent is extended or adjusted under 35 U.S.C. 154(b) by 0 days.

(21) Appl. No.: 10/796,777

(22) Filed: Mar. 9, 2004

(65) Prior Publication Data

US 2005/0201987 A1 Sep. 15, 2005

(51) Int. Cl.
*A61F 2/28* (2006.01)
*A61K 31/40* (2006.01)

(52) U.S. Cl. .................... 424/423; 514/408
(58) Field of Classification Search .................... None
See application file for complete search history.

(56) References Cited

U.S. PATENT DOCUMENTS

| | | | | |
|---|---|---|---|---|
| 4,610,692 | A | * 9/1986 | Eitenmuller et al. | 424/422 |
| 4,613,577 | A | 9/1986 | Tagai et al. | 501/35 |
| 4,976,736 | A | 12/1990 | White et al. | 623/16 |
| 5,108,436 | A | 4/1992 | Chu et al. | 623/66 |
| 5,207,710 | A | 5/1993 | Chu et al. | 623/16 |
| 5,423,919 | A | * 6/1995 | Dieter et al. | 134/8 |
| 5,468,544 | A | 11/1995 | Marcolongo et al. | 428/224 |
| 5,861,176 | A | 1/1999 | Ducheyne et al. | 424/486 |
| 5,871,777 | A | 2/1999 | Ducheyne et al. | 424/486 |
| 5,874,109 | A | 2/1999 | Ducheyne et al. | 424/486 |
| 6,054,400 | A | 4/2000 | Brink et al. | 501/63 |
| 6,180,606 | B1 | * 1/2001 | Chen et al. | 514/12 |
| 6,197,342 | B1 | 3/2001 | Thut et al. | 424/484 |
| 6,328,990 | B1 | 12/2001 | Ducheyne et al. | 424/426 |
| 6,632,412 | B2 | 10/2003 | Peltola et al. | 423/338 |
| 6,730,129 | B1 | * 5/2004 | Hall | 623/23.57 |
| 6,926,903 | B2 | * 8/2005 | Pirhonen et al. | 424/426 |
| 6,969,303 | B1 | * 11/2005 | Rolle et al. | 451/38 |
| 2003/0104029 | A1 | * 6/2003 | Pirhonen et al. | 424/426 |
| 2004/0115238 | A1 | 6/2004 | Laurencin et al. | 424/423 |
| 2004/0152627 | A1 | * 8/2004 | Weber | 514/12 |

FOREIGN PATENT DOCUMENTS

| | | |
|---|---|---|
| EP | 1 317 935 | 6/2003 |
| WO | WO 86/04088 | 7/1986 |
| WO | WO 97/31661 | 9/1997 |
| WO | WO 02/087647 | 11/2002 |
| WO | WO 03/065996 | 8/2003 |

OTHER PUBLICATIONS

Biocompatible ceramics, Cornell class notes, (www.mse.cornell.edu/courses/engri119/Class_Notes/biocompatible_ceramics.html), 2 pages attached, Mar. 6, 2006.*
Gombotz et al., "Stimulation of bone healing by transforming growth factor-1 released from polymeric or ceramic implants," *J. App. Biomat.*, 5:141-150 (1994).
Kokubo et al., "Apatite Formation on Surfaces of Ceramics . . . ," *Acta mater.*, 46,(7):2519-2527 (1998).
Peltola et al., "Effect of aging time of sol on structure and *in vitro* calcium phosphate formation of sol-gel-derived titania films," *J. Biomed. Mater. Res.*, 51(2):200-208 (2000).
Reddi, "Bone morphogenetic proteins . . . " *Cytokine & Growth Factor Reviews*, 8:11-20 (1997).
Rose and Oreffo, "Bone tissue engineering . . ." *Biochem. Biophys. Res. Com.*, 292:1-7 (2002).
Santos et al., Si-Ca-P xerogels and bone morphogenetic protein act synergistically on rat stromal marrow cell differentiation *in vitro*, *J. Biomed. Mater. Res.*, 41(1):87-94 (1998).
Weber et al., "Slow and continuous application of human recombinant bone morphogenetic protein via biodegradable poly(lactide-co-glycolide) foamspheres," *Intl. J. Oral Maxillofac. Surg.*, 31:60-65 (2002).
Wei et al., "Hydroxyapatite-Zirconia Functionally Graded Bioceramics Prepared by Hot Isostatic Pressing," *Key Engineering Materials*, 240 to 242:591-594 (2003).
Wozney and Rosen, "Bone morphogenetic protein and bone morphogenetic protein gene family in bone formation and repair," *Clin. Orthop. Rel. Res.*, 346:26-37 (1998).
Wozney et al., "Novel regulators of bone formation . . .," *Science*, 242:1528-1534 (1988).
Andriano et al., "Preliminary *In Vivo* Studies on the Osteogenic Potential of bone Morphogenetic Proteins Delivered from an Absorbable Puttylike Polymer Matrix," *Appl. Biomater.*, 53:36-43 (2000).
Wozney "Bone Morphogenetic Proteins," *Progress in Growth Factor Research*, 1:267-280 (1989).

* cited by examiner

*Primary Examiner*—Robert A. Wax
*Assistant Examiner*—Anand Desai
(74) *Attorney, Agent, or Firm*—Banner & Witcoff, Ltd.

(57) ABSTRACT

A bone grafting material, a method of producing the same, and an implant. The bone grafting material comprises a porous carrier of ceramic or glass ceramic or glass material and at least one pyrrolidone arranged in the carrier.

18 Claims, 1 Drawing Sheet

BONE GRAFTING MATERIAL, METHOD AND IMPLANT

JOINT RESEARCH AGREEMENT

The invention claimed herein was made by or on behalf of Inion, Ltd. and the University of Zurich who are parties to a joint research agreement. The agreement was executed by the University of Zurich on Feb. 1, 2003 and by Inion on Feb. 17, 2003. The agreement came into effect on Feb. 17, 2003, before the date the claimed invention was made. The agreement concerns the field of bioactive materials for bone formation, and the claimed invention was made as a result of activities undertaken within the scope of the agreement.

FIELD OF THE INVENTION

The present invention relates to a bone grafting material comprising a porous carrier of ceramic or glass ceramic or glass material.

The present invention further relates to a method of producing a bone grafting material.

The present invention further relates to an implant comprising a porous ceramic or glass ceramic or glass material.

BACKGROUND OF THE INVENTION

In surgical and orthopedic treatments, prosthesis operations are often required for filling in defects or hollow portions of bone which may result from a fracture of bone or a surgical removal of a bone tumor. Also in the field of dental surgery, similar dental operations are often required for filling in spoiled void portions in maxilla or mandible resulting from pyorroea alveolaris. It has been a common practice to harvest bone from a donor site, for example from the iliac crest of the patient, to fill up the defect or hollow portion of bone and thereby to promote the regeneration of the bone tissue. However, to perform such an operation, normal, undamaged bone tissue must be taken up from an unspoiled portion. This operation causes additional pain to the patient and is, in addition, a very troublesome procedure. Moreover, when the volume of the defect or void in the patient's bone is large, the amount of bone obtainable from the patient's own body is not always adequate to fully fill in the defect or void. In such cases, it is inevitable to use a substitute for the patient's own bone tissue.

Even though the same sort of bone tissue has been used as the substitute, the implanted substitute may be rejected by the living tissue due to the foreign body rejection reaction (by the immune system). For these reasons, post-operation recovery of the defect is not always satisfactory. Accordingly, such an operation has not yet been recognized as fully satisfactory in practice.

In recent years, intensive studies have been made on artificial materials called biomaterials to be introduced in the human body for repairing damages therein. A variety of metal alloys and organic materials have been used as the substitute for the hard tissues in the living body. However, it has been recognized that these materials tend to dissolve or otherwise deteriorate in the environment of living tissue and that these materials are toxic to the living body and cause a so called foreign body rejection reaction. Ceramic materials have been used because of their excellent compatibility with the living body and because they are typically free of the aforementioned difficulties. Artificial bones and teeth have been developed from ceramic materials, particularly alumina, carbon or tricalcium phosphate or from sintered masses or single crystal of hydroxyapatite which have superior compatibility with the living body. These embodiments have attracted a good deal of public attention. However, the conventional ceramic materials have a disadvantage in that the bone formation activity or bone filling process is relatively slow.

An acceleration of this bone filling process can be achieved by the principle of osteoconduction if an empty space is filled with porous materials which serve as a scaffold for the newly formed bone [Reddi, H., Cytokine & Growth Factor Reviews 8 (1997) 11 to 20]. Alternatively, bone repair can be accelerated by osteoinduction, which involves the application of appropriate growth factors capable of differentiating mesenchymal stem cells to osteoblasts [Wozney, J. M. and Rosen, V., Clin Orthop Rel Res 346 (1998) 26 to 37].

The most useful growth factors in osteoinduction are bone morphogenetic proteins (BMPs), which are differentiation factors and have been isolated based on their ability to induce bone formation [Wozney, J. M., et al., Science 242 (1988) 1528 to 534]. They build a BMP family with more than thirty members belonging to a TGF-$\beta$-super-family. The BMP family is divided to subfamilies including the BMPs, such as BMP-2 and BMP-4, osteogenic proteins (OPs), such as OP-1 or BMP-7, OP-2 or BMP-8, BMP-5, BMP-6 or Vgr-1, cartilage-derived morphogenetic proteins (CDMPs), such as CDMP-1 or BMP-14 or GDF-5, growth/differentiation factors (GDFs), such as GDF-1, GDF-3, GDF-8, GDF-9, GDF-11 or BMP-11, GDF-12 and GDF-14, and other subfamilies, such as BMP-3 or osteogenin, BMP-9 or GDF-2, and BMP10 (Reddi et al., 1997, supra).

Especially in animal models, the BMPs have proved to be powerful inducers of bone formation and repair. However, due to the instant degradation of the BMPs upon contact with body fluids and the strong morphogenetic action of the BMPs, un-physiologically high doses of the BMPs are needed for the osteoinductive bioactivity [Weber, F. E., et al., Int J Oral Maxillofac Surg 31 (2002) 60 to 65; Rose, F. R. A. and Oreffo, R. O. C. Biochem Biophys Res Corn 292 (2002) 1 to 7]. Topical administration routes must be used, which makes the choice of the carrier system critical, and no suitable carrier systems are currently available. Since the BMPs are usually produced with recombinant techniques and thus are expensive and available only in limited amounts, the BMPs, despite the acknowledged effect, have had no impact on the medical treatment of patients and they are not clinically applied at present.

BRIEF DESCRIPTION OF THE INVENTION

An object of the present invention is to provide a novel bone grafting material, implant and method of producing a bone grafting material so as to alleviate the above disadvantages.

The objects of the invention are achieved by a bone grafting material, a method of producing a bone grafting material and an implant, which are characterized by what is stated in the independent claims. Preferred embodiments of the invention are disclosed in the dependent claims.

The bone grafting material of the invention is based on the idea that it comprises a porous carrier of ceramic or glass ceramic or glass material and at least one pyrrolidone arranged in the carrier.

The method of the invention of producing a bone grafting material is based on the idea the method comprises the step of making a porous carrier of ceramic or glass ceramic or glass material, and adding at least one pyrrolidone to the porous carrier.

The implant of the invention is based on the idea that it comprises a carrier of porous ceramic or glass ceramic or glass material and at least one pyrrolidone arranged in the carrier.

An advantage of the invention is that the administration of pyrrolidone enhances and accelerates the formation of new bone or cartilage tissue.

In one embodiment of the invention, the bone grafting material comprises at least one bone morphogenetic protein (BMP). An advantage of the embodiment is that the administration of BMPs in combination with a pyrrolidone enhances bone formation in a synergistic manner. This affords advantages in terms of smaller amounts of the material needed for the desired effect, which is of great importance in view of the laborious production of especially recombinant BMPs (rBMPs) in particular. Also, the risk of side effects decreases significantly when smaller amounts of foreign material can be used.

In another embodiment of the bone grafting material of the invention, the porous carrier is of calcium phosphate ceramics (CPCs), such as hydroxyapatite (HA), β-tricalcium phosphate (β-TCP) and Brushite.

In another embodiment of the bone grafting material of the invention, the porous scaffold is manufactured by sintering bioactive glass fibers which is further immersed into a simulated body fluid (SBF) in order to create a carrier of CaP and a Si-rich layer on the glass surface. The pyrrolidone is applied to the CaP—Si-layer prior to implanting the material into a bone defect.

In one embodiment of the method of the invention of producing a bone grafting material an anorganic mineral bone matrix of bovine origin is loaded with pyrrolidone prior to implantation.

In one embodiment of the implant of the invention, the material of the implant is a biopolymer-bioceramic composite that is processed by extrusion, injection molding or an other manufacturing method, and prior to manufacturing the composite, the porous bioceramic is loaded with pyrrolidone.

In one embodiment of the invention, a metallic hip implant that has a porous bioceramic coating on its surface is loaded with pyrrolidone prior to implantation.

BRIEF DESCRIPTION OF THE DRAWINGS

In the following, the invention will be described in greater detail by means of preferred embodiments and with reference to the accompanying drawings, in which.

DETAILED DESCRIPTION OF THE INVENTION

Figure 1:
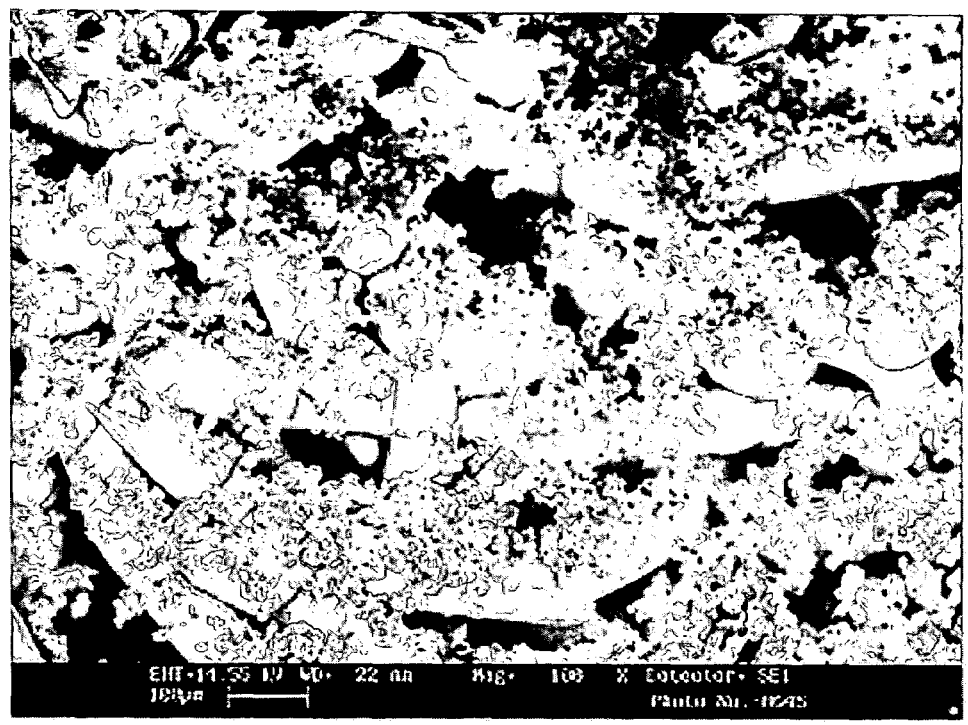
FIG. 1 and FIG. 2 show a structure of a porous scaffold for a bone grafting material according to the invention.
Figure 2:
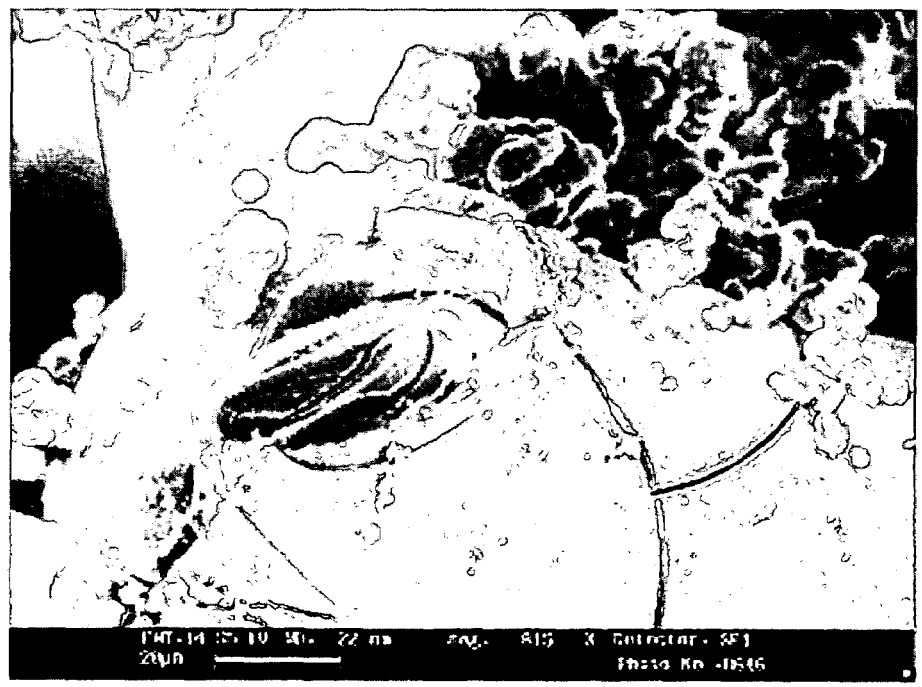

FIG. 1 (110× magnification) and FIG. 2 (850× magnification) show a structure of a porous scaffold that is formed by sintering bioactive glass fibres and further immersing the scaffold into a simulated body fluid (SBF) in order to achieve a porous CaP/Si layer on top of the glass surface. Bioactive glass was made of composition A (see table 1).

It should be noted here that a bioceramic is any ceramic, glass or glass ceramic that is used as a biomaterial and which upon implantation is transformed into less soluble minerals.

A bioactive material is a material that can bond to living tissue, such as bone or cartilage.

A carrier is a porous structure that can absorb polypyrrolidone.

A scaffold is a porous or non-porous structure that serves as a base or substrate for the carrier.

EXAMPLE 1

Two batches of bioactive glasses with compositions shown in Table 1 were first formed by melting the raw-materials in Pt-Au crucible for 2 to 3 hours at approximately 1360° C.

TABLE 1

The composition of the bioactive glasses [wt-%].

| Glass | $Na_2O$ | $K_2O$ | MgO | CaO | $B_2O_3$ | $P_2O_5$ | $SiO_2$ |
|---|---|---|---|---|---|---|---|
| A | 18 | 9 | 0 | 14 | 1 | 4 | 54 |
| B | 12 | 15 | 5 | 11 | 1 | 2 | 54 |

From both batches of the bioactive glasses, fibers with a diameter of approximately 75 μm were then formed by melt spinning. The fibers were further cut to have a segment length of approximately 3 mm. From the obtained fibre segments were formed 3-dimensional scaffolds with open network. The forming took place by first placing the fibre segments in a mould and then sintering the fibers at elevated temperatures.

The obtained scaffolds were then immersed into a simulated body fluid for a one-week period in order to obtain a formation of Si-rich layer and calcium phosphate (CaP) precipitation on the surface of the scaffolds. Scaffolds containing a CaP surface as a carrier layer were then flushed with water and dried first in air for approximately 24 hours and then in a vacuum oven for approximately 24 hours. The masses of the scaffolds were measured with a balance. The scaffolds were then placed in a chamber with a total capacity of 10 $dm^3$ and having one $dm^3$ of 1-methyl-2-pyrrolidone (NMP) in the bottom of the chamber. The scaffolds were placed on top of a metallic stay, which was placed over the NMP liquid. The chamber was closed tightly, and the air was removed from the chamber with a vacuum pump in order to achieve NMP to vaporize inside the chamber. In order to study the amount of NMP absorbed into the material, the masses of the materials were measured after 1, 3, 5 and 7 days of storage in the chamber. The NMP uptake for materials is shown in Table 2.

TABLE 2

The amount of NMP in scaffold/carrier structures.

| Sample No. | NMP in structure after 1 day [wt-%] | NMP in structure after 3 days [wt-%] | NMP in structure after 5 days [wt-%] | NMP in structure after 7 days [wt-%] |
|---|---|---|---|---|
| A1 | 1.360 | 1.447 | 1.274 | 1.575 |
| A2 | 1.867 | 1.531 | 1.611 | 1.954 |
| A3 | 1.705 | 1.445 | 1.525 | 1.670 |
| Average | 1.644 | 1.474 | 1.470 | 1.733 |
| Std. dev. | 0.259 | 0.049 | 0.175 | 0.197 |
| B1 | 0.965 | 3.215 | 4.148 | 4.548 |
| B2 | 1.487 | 3.891 | 4.298 | 5.467 |
| B3 | 1.361 | 6.958 | 7.486 | 8.117 |
| Average | 1.271 | 4.688 | 5.311 | 6.044 |
| Std. dev. | 0.272 | 1.995 | 1.886 | 1.853 |

The amount of NMP absorbed into the structure with composition "A" reaches approximately 1.7 wt-% of the total weight of the structure and the amount of NMP absorbed into structure with composition "B" reaches approximately 6 wt-% of the total weight of the structure within 7 days.

Pyrrolidone can be vaporized not only by dropping the pressure of the vaporizing chamber but also by raising the temperature of the vaporizing chamber high enough.

Suitable porous carriers useful in the present invention include bioceramics capable of adsorbing a sufficient amount of one or more pyrrolidones. Preferably, the porous carrier has a high surface energy and a large specific surface area. The porous carrier can be, for example, calcium phosphates, hydroxy apatites, silica gels, sol-gel glass, anorganic mineral bone matrixes, xerogels, ceramic-polymer composites, such as hydroxy apatite/polyethylene composites, tricalsium phosphate/polylactide, CaP/polyurethane, bioglass/polylactide or any other biopolymer composite which contains a porous bioceramic phase.

The scaffold can also be a bioactive glass in crushed form or as spherical granules. This kind of bioactive glass is disclosed, for example, in U.S. Pat. No. 6,054,400.

Another method of obtaining porous carriers useful in the present invention is to use a sol-gel method. A pyrrolidone can be implemented into the ceramic sol-gel derived material already in the manufacturing phase, as described in U.S. Pat. Nos. 5,861,176, 5,871,777 and 5,874,109, which are hereby incorporated by reference in their entirety for all purposes.

Another method is to create a porous ceramic coating onto a biomedical implant with a dipping method, as described in "Effect of aging time of sol on structure and in vitro calcium phosphate formation of sol-gel-derived titania films", Peltola et al., J Biomed Mater Res. 2000 August; 51(2): 200 to 208. The sol-gel coating in an implant can be further loaded with pyrrolidone or pyrrolidones.

Another method of obtaining porous carriers useful in the present invention is to use the porous bioactive fibers manufactured with sol-gel method as described in U.S. Pat. No. 6,632,412, which is hereby incorporated by reference in its entirety for all purposes. These porous fibers can be further loaded with pyrrolidone or pyrrolidones e.g. using a vacuum chamber as described in Example 1.

The scaffold can also comprise calcium carbonate which as a carrier has a surface layer of a synthetic phosphate, such as hydroxyapatite. Such a structure is disclosed, for example, in U.S. Pat. No. 4,976,736, which is hereby incorporated by reference in its entirety for all purposes.

Another possible scaffold or carrier material is a xerogel glass. For example, Santos et al. describe xerogel glass as a carrier for a bone morphogenetic protein (BMP). The carrier releases functional bone growth factors in a sustained manner over a period of several weeks [J. Biomed. Mater. Res. (1998) July; 41(1):87 to 94].

U.S. Pat. No. 5,861,176 discloses carriers comprising silica-based glass provided for a controlled release of biologically active molecules. Biologically active molecules are incorporated in the matrix of the glass during production. The carriers are prepared using a sol-gel-derived process. Pyrrolidone can be implemented into a porous sol-gel-material using methods similar to those described in U.S. Pat. No. 5,861,176, which is hereby incorporated by reference in its entirety for all purposes.

The bone grafting material according to the present invention can be carried out as a carrier with no scaffold structure. For example, a bone grafting material consisting of CaP loaded with pyrrolidone can be accomplished. Also hydroxy apatites, silica gels, sol-gel glass, anorganic mineral bone matrixes, xerogels, ceramic-polymer composites, such as hydroxy apatite/polyethylene composites, tricalsium phosphate/polylactide, CaP/polyurethane, bioglass/polylactide or any other biopolymer composite which contains a porous bioceramic phase can be carried out with no scaffold structure.

The pyrrolidones useful in the present invention are include any pyrrolidone known in the art of chemistry to have a plastizising or solubilizing properties without having tissue impairing effects or toxic effects. Such pyrrolidones include, for example, alkyl- or cycloalkyl-substituted pyrrolidones, such as 1-methyl-2-pyrrolidone (NMP), 1-ethyl-2-pyrrolidone (NEP), 2-pyrrolidone (PB), and 1-cyclohexyl-2-pyrrolidone (CP), NMP and NEP being preferred examples. Additionally, pyrrolidone-based polymers, such polyvinylpyrrolidones, may also be useful in the material of the invention. Preferably, pyrrolidone is bound to the carrier by a chemical bond, e.g. ionic or electrostatic bond.

Surprisingly it was discovered that the administration of a pyrrolidone in combination with ceramic bone grafting materials may result in a quicker bone formation process.

EXAMPLE 2

Six pieces of bone grafting material comprising a porous bioactive glass scaffold "A" or "B" (the compositions being the same as in Example 1) and with a CaP layer on top of the glass surface were manufactured as described in example 1. All the samples were weighed with a top balance and the samples were then placed into a high-pressure chamber (with a total volume of 0.37 dl) together with 2 ml of NMP. The samples were placed on a metallic sample holder. The high-pressure chamber was closed and the chamber was first filled with a $CO_2$ vapor at room temperature. The chamber was then heated to a temperature of 60° C. so that the pressure inside the chamber increased up to 120 bar. These conditions were remained for 24 hours, and the pressure was lowered slowly within 15 minutes to reach a normal air pressure. The weight of the samples was then measured.

TABLE 3

The amount of NMP in scaffold/carrier structures.

| Sample No. | Initial weight [g] | Weight after treatment [g] | Weight-% of NMP |
|---|---|---|---|
| A1 | 0.3676 | 0.3731 | 1.49 |
| A2 | 0.2677 | 0.2733 | 2.10 |
| B1 | 0.3872 | 0.3911 | 0.99 |
| B2 | 0.2983 | 0.3001 | 0.60 |

EXAMPLE 3

Various bioceramics and one bioceramic composite were acquired, namely
1) Synthetic calcium phosphate (CaP), 3-dimensional scaffold manufactured by sintering CaP powder,
2) Bio-Oss®, an anorganic mineral bone matrix of bovine origin, and
3) Hydroxyapatite (HA) powder with a particle size of 4 μm.

The samples were dried in a vacuum and further placed in a chamber containing 1-methyl-2-pyrrolidone (NMP) as described in Example 1. The masses of the samples were monitored prior to placing them in a chamber and 5 and 7 days after the placement in the chamber. The amount of absorbed NMP as weight-% is shown in Table 4.

TABLE 4

The absorption of NMP.

| Sample No. | NMP in structure after 5 days [wt-%] | NMP in structure after 7 days [wt-%] |
|---|---|---|
| 1 | 0.69 | 1.06 |
| 2 | 32.24 | 39.20 |
| 3 | 0.16 | 0.23 |

Table 4 shows that the absorbtion of NMP varies significantly depending on the composition and structure of the bioceramic material. The highest amount of NMP was absorbed by Bio-Oss, approximately 40 wt-%. Sintered CaP scaffold absorbed approximately 1 wt-% of NMP and the particulate HA absorbed 0.2 wt-% of NMP.

According to certain aspects of the present invention, the bone grafting material of the present invention includes pyrrolidone in an amount between about 0.1 and about 50 wt-%, more preferably between about 1 and about 20 wt-% of the total weight of the porous pyrrolidone loaded carrier.

The carrier can be a composite material comprising a ceramic part and a polymer part. Potentially suitable carriers are described, for example, in U.S. Pat. Nos. 5,468,544 and 6,328,990, which are hereby incorporated by reference in their entirety for all purposes. U.S. Pat. No. 5,468,544 discloses composite materials using a bone bioactive glass and ceramic fibers. In more detail, the patent discloses composite structures that incorporate a bioactive material in to a polymer matrix along with a structural fiber. The polymeric matrix used is a non-bioabsorbable polymeric matrix, for example polysulphone (PSU), Polyether-etherketone (PEEK) or Polyether-ketone-ketone (PEKK), and the structural fiber is a carbon fiber. U.S. Pat. No. 6,328,990 discloses a bioactive, degradable composite material where the composite is made by mixing a modified bioactive glass powder with a poly (lactic-co-glycolic acid) polymer matrix.

The carrier may also consist of a porous body of joined-together particles of a comminuted porous sintered glass fibre matrix. For example WO 86/04088 discloses such carriers for immobilising active materials, such as enzymes and microorganisms. Preferably, a carbonized organic binder, such as polyacrylate, polyvinyl acetate and polyvinyl acetal, holds the particles together at the points of contact with one another.

Still another suitable carrier may be a composite implant made from a poly(lactide-co-glycolic acid) and demineralized bone matrix. [Gombotz et al., J. App. Biomat., (1994) 5: 141 to 150]

EXAMPLE 4

Six pieces of bone grafting material comprising a porous bioactive glass scaffold "A" or "B" (the compositions being the same as in Example 1) and with a CaP layer on top of the glass surface were manufactured as described in Example 1. All the samples were weighed with a top balance. Group I samples were then placed individually in aluminum pouches. Into each pouch, five drops of NMP was further added in order to let the NMP absorb into the bone grafting materials. After adding the NMP the pouches were tightly closed with heat seal, in order to avoid any diffusion of liquids or gasses through a pouch or a seal. The samples were stored at normal room conditions for five days. After five days of storage, the pouches were opened and the masses of the samples were measured. The results of the initial mass and the mass after storage are shown in Table 5.

TABLE 5

The weight of bone grafting materials prior and after absorption of NMP.

| Sample No. | Initial weight [g] | Weight after storage [g] | Amount of NMP [%] |
|---|---|---|---|
| A.I.1 | 0.179 | 0.182 | 1.541 |
| A.I.2 | 0.391 | 0.395 | 1.020 |
| A.I.3 | 0.302 | 0.307 | 1.533 |
| Average | | | 1.365 |
| Std. dev. | | | 0.298 |
| B.I.1 | 0.293 | 0.296 | 1.010 |
| B.I.2 | 0.279 | 0.282 | 1.227 |
| B.I.3 | 0.306 | 0.311 | 1.603 |
| Average | | | 1.280 |
| Std. dev. | | | 0.300 |

As can be seen in Table 5, the NMP can be loaded into the carrier also by placing the bone grafting material in a pouch that contains few drops of NMP. With the dipping method in the carrier absorbs NMP but the bone grafting material also contains NMP as liquid form inside the structure.

The bone grafting material of the invention can be used as such in surgical, orthopaedic and dental treatments. In one embodiment of the invention, the material of the invention is incorporated in a pre-formed implant. The implant can be, for example, a hip joint prosthesis which comprises a coating made of the bone grafting material of the invention in order to ensure a secure bonding of the prosthesis to femur. The material of the invention may possess a similar function also in a knee joint implant or similar joint prosthesis. The implant may also be a dental implant whose root surface is coated with the bone grafting material of the invention. Additionally, the implant may be a GBR (Guided Bone Regeneration) film or sheet preferably made of ceramic fibers or composites.

The implant materials or scaffolds which may be coated with the invented materials include ceramic, metal and polymeric implants, e.g. metallic joint implants e.g. hip and knee implants or similar implants.

One possibility is to use the method by Kokubo et al. wherein body like medium is used to get nucleated apatite on ceramic, metal or polymer surfaces which contain Si—OH, Ti—OH and/or Ta—OH groups. These groups induce the apatite nucleation. Kokubo et al. have formed bone like apatites on metals, such as silicon, titanium and its alloys, tantalum and organic polymers, such as poly(ethylene terephtalate), polyether sulfone and polyethylene [Kokubo et al., Acta mater., 46, 7: (1998) 2519 to 2527].

Another method which may be used to coat ceramic materials in particular is hot isostatic pressing. An example of this method is described by Wei et al., who describe a process wherein hydroxyapatite-zirconia biomaterials were prepared by hot isostatic pressing at 1100° C. under a pressure of 140 MPa [Wei et al. Key Engineering Materials, 240 to 242: (2003) 591 to 594].

Still another method which may be used to coat a scaffold with the bone grafting material according to the invention is electrochemical coating. For example, Becker et al. describe a method of coating titanium with a composite of CaP-phases Brushite with less Hydroxyapatite (Bonit®).

A metal implant can also be coated by sputtering the bone grafting material on the implant.

Further, a sol-gel-derived process disclosed in U.S. Pat. No. 5,861,176 may be used to coat, for example, a silica-based glass scaffold.

Still another method which may be used to coat a scaffold with the bone grafting material according to the invention is described in U.S. Pat. Nos. 5,108,436 and 5,207,710, which are hereby incorporated by reference in this entirety for all purposes. These methods include coating, saturation, applying a vacuum force to get the material into the pores, air drying or freeze drying the material onto the scaffold.

The bone grafting material of the invention may include a biologically active substance or agent providing an extended therapeutical effect. The biologically active agent can be selected from the group consisting of anti-inflammatory agents, antibacterial agents, antiparasitic agents, antifungal agents, antiviral agents, anti-neoplastic agents, analgesic agents, anaesthetics, vaccines, central nervous system agents, growth factors, hormones, antihistamines, osteoinductive agents, cardiovascular agents, anti-ulcer agents, bronchodilators, vasodilators, birth control agents, fertility enhancing agents and polypeptides. Preferably, the bioactive agents are bone morphogenic proteins (BMP), such as OP-1, BMP-2, BMP4, BMP-6 and BMP-7.

It will be obvious to a person skilled in the art that as the technology advances, the inventive concept can be implemented in various ways. The invention and its embodiments are not limited to the examples described above but may vary within the scope of the claims.

The invention is:

1. A bone grafting material comprising a porous carrier of ceramic or glass ceramic or glass or ceramic/polymer composite, and at least one pyrrolidone, wherein the pyrrolidone is selected from the group consisting of 1-methyl-2-pyrrolidone (NMP), 1-ethyl-2-pyrrolidone (NEP), 2-pyrrolidone (PB) and 1-cyclohexyl-2-pyrrolidone (CP).

2. The bone grafting material of claim 1, wherein the pyrrolidone is bound to the carrier by a chemical bond.

3. The bone grafting material of claim 1, wherein the pyrrolidone is 1-methyl-2-pyrrolidone (NMP).

4. The bone grafting material of claim 1, wherein the amount of pyrrolidone is between about 0.1 and about 50 weight-% of the total weight of the pyrrolidone loaded porous carrier.

5. The bone grafting material of claim 1, wherein the carrier is selected from the group consisting of calcium phosphates, hydroxy apatites, silica gels, anorganic mineral bone matrixes, xerogels and sol-gel glasses.

6. The bone grafting material of claim 1, wherein the polymer is selected from the group consisting of polysulphones, polyaryletherketones, polyolefins and biodegradable polymers.

7. A bone grafting material comprising a porous carrier including calcium phosphate and 1-methyl-2-pyrrolidone (NMP).

8. An implant comprising a carrier of porous ceramic or glass ceramic or glass, and at least one pyrrolidone, wherein the pyrrolidone is selected from the group consisting of 1-methyl-2-pyrrolidone (NMP), 1-ethyl-2-pyrrolidone (NEP), 2-pyrrolidone (PB) and 1-cyclohexyl-2-pyrrolidone (CP).

9. The implant of claim 8, wherein the amount of pyrrolidone is between about 0.1 and about 50 weight-% of the total weight of the pyrrolidone loaded porous carrier.

10. The implant of claim 8, wherein the implant comprises a scaffold, and wherein the carrier is present on a surface of the scaffold.

11. The implant of claim 10, wherein the scaffold is made of ceramic or glass ceramic or glass.

12. The implant of claim 10, wherein the scaffold is made of metal.

13. The implant according to claim 10, wherein the scaffold is made of a polymer.

14. The implant of claim 10, wherein the scaffold is porous.

15. The implant of claim 8, wherein the carrier is selected from the group consisting of calcium phosphates, hydroxy apatites, silica gels, anorganic mineral bone matrixes, xerogels and sol-gel glasses.

16. The implant of claim 8, wherein the carrier comprises a ceramic/polymer composite.

17. The implant of claim 16, wherein the polymer is selected from the group consisting of polysulphones, polyaryletherketones, polyolefins and biodegradable polymers.

18. . An an implant having a surface and a bone grafting material coated on said surface,
    wherein the bone grafting material comprises a carrier of porous ceramic or glass ceramic or glass, and at least one pyrrolidone, wherein the pyrrolidone is selected from the group consisting of 1-methyl-2-pyrrolidone (NMP), 1-ethyl-2-pyrrolidone (NEP), 2-pyrrolidone (PB). and 1-cyclohexyl-2-pyrrolidone (CP).

* * * * *